(12) United States Patent
Dorsey et al.

(10) Patent No.: US 11,813,321 B2
(45) Date of Patent: Nov. 14, 2023

(54) VACCINES AGAINST AVIAN REOVIRUSES

(71) Applicant: Biomune Company, Lenexa, KS (US)

(72) Inventors: Kristi Mae Dorsey, Shawnee, KS (US); Brianna Ford, Lawrence, KS (US); Christopher Luther, Lenexa, KS (US); John Knox Rosenberger, Lincoln University, KS (US)

(73) Assignee: BIOMUNE COMPANY, Lenexa, KS (US)

( * ) Notice: Subject to any disclaimer, the term of this patent is extended or adjusted under 35 U.S.C. 154(b) by 336 days.

(21) Appl. No.: 17/259,798

(22) PCT Filed: Jul. 12, 2019

(86) PCT No.: PCT/IB2019/055956
§ 371 (c)(1),
(2) Date: Jan. 12, 2021

(87) PCT Pub. No.: WO2020/012428
PCT Pub. Date: Jan. 16, 2020

(65) Prior Publication Data
US 2021/0308253 A1 Oct. 7, 2021

Related U.S. Application Data

(60) Provisional application No. 62/697,773, filed on Jul. 13, 2018.

(51) Int. Cl.
| | | |
|---|---|---|
| *A61K 39/15* | (2006.01) | |
| *C12N 7/00* | (2006.01) | |
| *A61P 31/14* | (2006.01) | |
| *A61P 37/04* | (2006.01) | |
| *A61K 39/00* | (2006.01) | |

(52) U.S. Cl.
CPC .............. *A61K 39/15* (2013.01); *A61P 31/14* (2018.01); *A61P 37/04* (2018.01); *C12N 7/00* (2013.01); *A61K 2039/5252* (2013.01); *A61K 2039/545* (2013.01); *A61K 2039/552* (2013.01); *A61K 2039/55555* (2013.01); *C12N 2720/12221* (2013.01); *C12N 2720/12234* (2013.01); *C12N 2720/12271* (2013.01)

(58) Field of Classification Search
None
See application file for complete search history.

(56) References Cited

U.S. PATENT DOCUMENTS

| | | | |
|---|---|---|---|
| 2016/0144037 A1 | 5/2016 | Miller et al. | |
| 2016/0279237 A1* | 9/2016 | Miller | A61K 39/0258 |
| 2018/0326043 A1* | 11/2018 | Pouwels | A61K 39/15 |
| 2021/0308253 A1* | 10/2021 | Dorsey | A61P 37/04 |

FOREIGN PATENT DOCUMENTS

| | | |
|---|---|---|
| WO | 2008/157659 A1 | 12/2008 |
| WO | 2016/050961 A1 | 4/2016 |
| WO | 2016/086222 A1 | 6/2016 |
| WO | 2017/081232 A1 | 5/2017 |

OTHER PUBLICATIONS

Sellers (Avain Diseases. 2022; 66: 420-426).*
Dawe et al. (Avian Diseases. 2022; 66: 465-478).*
Markis (Avian Diseases. 2022; 66: 435-442).*
Gabrone et al. (Journal of Applied Poultry Research. 2007; 16: 187-191).*
International Search Report and Written Opinion for corresponding PCT application No. PCT/IB2019/055956 dated Oct. 9, 2019.
Avishai L. et al., "Wide-range protection against avian reovirus conferred by vaccination with representatives of four defined genotypes.", Vaccine, Elsevier, Amsterdam, NL, vol. 29, No. 47, Aug. 25, 2011, pp. 8683-8688.

* cited by examiner

*Primary Examiner* — Shanon A. Foley
(74) *Attorney, Agent, or Firm* — Wood, Phillips, Katz, Clark & Mortimer

(57) ABSTRACT

The present invention relates to vaccine and composition comprising at least one antigenic material derived from an avian reovirus and an adjuvant comprising a lipophile and a polymer of acrylic or methacrylic acid and uses thereof for vaccinating avian against reoviruses.

16 Claims, No Drawings

VACCINES AGAINST AVIAN REOVIRUSES

FIELD OF THE INVENTION

The present invention relates to new vaccines or compositions comprising at least one antigenic material derived from an avian reovirus and an adjuvant comprising a lipophile and a polymer of acrylic or methacrylic acid. The present invention also relates to new strains of avian reoviruses and vaccines or compositions comprising the same. The present invention is particularly suited to protect avian, such as poultry, from emerging reovirus diseases.

BACKGROUND OF THE INVENTION

Avian reoviruses (Respiratory Enteric Orphan Virus) are double-stranded RNA viruses that belong to the genus Orthoreovirus from the family Reoviridae. While reovirus infections of poultry are widespread and the majority of avian reoviruses cause asymptomatic infections, the pathogenic strains of virus are one of the major causes of economic losses in the poultry industry. The most frequent disease caused by avian reovirus is viral arthritis (tenosynovitis). The main clinical symptom of viral arthritis is swelling of chicken's hock joints causing leg weakness and lameness. Avian reoviruses also have been associated with a number of poultry diseases such as myocarditis, hepatitis, malabsorption as well as enteric and respiratory problems. Reovirus infections affect predominantly meat type poultry (broilers) and result in poor growth of affected chickens through their inability to compete for feed with the healthy chickens.

Vaccination is a main control measure used against poultry diseases caused by reoviruses. The vaccination approach usually involves active and passive immunity, which is achieved by administering live vaccine to young chicks followed by administration of an inactivated vaccine to older chickens with intention to protect the progeny of the vaccinated chickens with maternal antibodies. Current vaccines are not always satisfactory due to efficacy issues as well as to the emergence of new virulent avian reovirus strains.

There is thus a need for new efficacious reovirus vaccines.

SUMMARY OF THE INVENTION

The present invention provides new vaccines against reovirus(es). More particularly, the invention provides new vaccines which contain reovirus antigen(s) and a particular adjuvant system which, in combination, induce potent immune responses and may be used to protect against emergent virulent strains. The invention also provides new vaccines combining several strains of particular serotypes, which induce potent immune protection.

An object of the present invention therefore resides in a vaccine comprising at least one antigenic material derived from an avian reovirus and an adjuvant comprising a lipophile and a polymer of acrylic or methacrylic acid.

Another object of the present invention relates to an avian reovirus strain designated S1, derived from serotype 1, a sample of which is deposited under PTA-125155, as well as derivatives thereof.

Another object of the present invention relates to an avian reovirus strain designated S2, derived from serotype 2, a sample of which is deposited under PTA-125157, as well as derivatives thereof.

Another object of the present invention relates to an avian reovirus strain designated S3, belonging to serotype 3, a sample of which is deposited under PTA-125156, as well as derivatives thereof.

Another object of the present invention relates to a vaccine comprising (i) at least one antigenic material derived from at least one avian reovirus selected from an avian reovirus of serotype 1, an avian reovirus of serotype 2, an avian reovirus of serotype 3, and any mixture thereof.

In a particular embodiment, the vaccine comprises (i) at least one antigenic material derived from an avian reovirus selected from strains S1, S2 or S3, and derivatives thereof, and (ii) an adjuvant composition.

Another object of the present invention relates to a vaccine comprising (i) at least one antigenic material derived from at least one avian reovirus selected from strain S1133, 2408, SS412, and any mixture thereof, and (ii) adjuvant comprising a lipophile and a polymer of acrylic or methacrylic acid.

The present invention also relates to a process for preparing a vaccine comprising at least one antigenic material derived from an avian reovirus and an adjuvant, comprising
  preparing the at least one antigenic material;
  optionally homogenously mixing the at least one antigenic material with glycine and/or thimerosal solutions, and
  adding an adjuvant comprising a lipophile and a polymer of acrylic or methacrylic acid.

In another aspect, the invention relates to a method for vaccinating an avian against reovirus or a reovirus-associated disease, comprising administering to the avian a vaccine as disclosed above.

The invention also provides a method for inducing an immunogenic or protective response in an avian against at least one reovirus, comprising administering to said avian a vaccine as disclosed above.

The invention also provides a method of protecting an avian, preferably poultry, against a disease or condition resulting from an avian reovirus infection, comprising the step of administering the vaccine as disclosed above to the avian.

Another object of the present invention relates to a vaccine or composition as disclosed above for use in a method for vaccinating an avian against reovirus or a reovirus-associated disease and/or for inducing an immunogenic or protective response in an avian against at least one reovirus and/or for protecting an avian, against a disease or condition resulting from an avian reovirus infection, wherein said method consists of the administration of a dose of said vaccine or composition to said avian. Preferably, said avian is a poultry.

A further aspect of the invention relates to a vaccination kit for immunizing an avian which comprises an effective amount of a vaccine as disclosed above and a means for administering said vaccine to said avian.

The invention also provides an isolated avian reovirus designated strain S1, a sample of which is deposited at the ATCC under accession number PTA-125155.

The invention also provides an isolated avian reovirus designated strain S2, a sample of which is deposited at the ATCC under accession number PTA-125157.

The invention also provides an isolated avian reovirus designated strain S3, a sample of which is deposited at the ATCC under accession number PTA-125156.

DETAILED DESCRIPTION OF THE INVENTION

The present invention is based on the combination of reovirus antigenic material and a particular adjuvant system which, together, provide efficient and safe vaccination. The present invention also relates to vaccines against avian reoviruses, which comprise antigenic material derived from several avian reoviruses.

The present disclosure will be best understood by reference to the following definitions:

Definitions

The term "avian reovirus" designates a virus belonging to the species avian Orthoreovirus (R. C. Jones "Avian reovirus infections" Rev. sci. tech. off. Int. Epiz., 2000, 19(2), 614-625).

The term "avian" is intended to encompass all kinds of avians, such as birds of the class of Ayes, i.e., vertebrate animals which are feathered, winged, bipedal, endothermic and egg-laying. In the context of the invention, avians or avian species refer more particularly to birds with economical and/or agronomical interests, such as poultry (such as chickens, turkeys, hens, guinea fowl, quail, partridge and pigeon), waterfowl poultry (such as ducks and geese) and ornamental birds (such as swans, parrot and psittacines).

The term "vaccine" as used herein designates an agent which may be used to cause, stimulate or amplify an immune response in an organism.

An "immune response" designates the development in a host of a cellular and/or antibody-mediated immune response. Usually, an "immune response" includes the production of antibodies, B cells, helper T cells, and/or cytotoxic T cells, directed specifically to an antigen or antigens of interest. Preferably, the immune response is protective such that resistance to new infection will be enhanced and/or the clinical severity of the disease reduced. For the vaccine according to the invention ("avian reovirus vaccine"), the immune response induced in the vaccinated target animal has for instance the effect of reducing infection by an avian reovirus. This refers to a reduction of the level or the extent of the infection, for example by reducing the viral load or shortening the duration of viral replication in the host animal. This effect is obtained e.g., by preventing or reducing the establishment or the proliferation of a productive infection by avian reovirus in its target organs such as tendon, or intestines. In turn this leads to a reduction in the target animal of the number, the intensity, or the severity of lesions and clinical signs that could be caused by the viral infection. The person skilled in the art is able to determine the effectiveness of a vaccine according to the invention for reducing infection by avian reovirus. For instance, this determination may be done by monitoring the immunological response following vaccination or after a challenge infection, e.g. by monitoring the targets' signs of disease, clinical scores, serological parameters, or by re-isolation of the pathogen, and comparing these results to a vaccination-challenge response seen in mock vaccinated animals.

Compositions or Vaccines

The present invention relates to compositions or vaccines comprising antigenic material(s) derived from at least one avian reovirus. Particularly, the present invention provides vaccines against reovirus combining antigenic material derived from at least one avian reovirus and a particular adjuvant. Indeed, the inventors have shown, for the first time, that an adjuvant comprising a lipophile and a polymer of acrylic or methacrylic acid is particularly suited for avian vaccines. The use of this adjuvant provides several advantages as compared to traditional water-in-oil adjuvant composition, such as ease to formulate, less injection site reaction, shorter withdrawal time, possibility to administer the vaccine to chicken of less than 18 weeks of age and good immunity response. Furthermore, the inventors have shown that the combination of such adjuvant with antigenic material derived from avian reovirus leads to an efficient and safe vaccine, that may be administered by the intra-muscular route.

The "antigenic material" can be any type of immunogenic material derived from an avian reovirus provided it can induce a protective immune response (either by itself or with an adjuvant). The antigenic material may be a replicative avian reovirus (e.g., a 'live' avian reovirus); an inactivated ('killed') avian reovirus, an attenuated avian reovirus; or a part thereof such as a subunit, extract, fraction, recombinant vector, homogenate or sonicate, for instance. The terms "killed" or "inactivated" refer to a significant or complete reduction in the infectivity of the virus(es). Typically, an inactivated virus is a virus which has been structurally altered and is unable to infect a cell. The term «attenuated reovirus» refers to a live reovirus capable of replication, which is not pathogenic. An attenuated reovirus can for instance contain an attenuating mutation which results in a decreased probability of causing disease in its host (i.e., a loss of virulence) in accordance with standard terminology in the field.

In the context of the invention, an antigenic material is "derived from" an avian reovirus if it can be obtained from an avian reovirus or from a part thereof or if it has a structure identical or similar to that of a material or component or element contained in an avian reovirus. Examples of ways to derive antigenic material from an avian reovirus may be to proliferate an avian reovirus strain in an appropriate host cell, after which the virus can be harvested and isolated by standard techniques well known in the art. The harvested replicative virus can be used as antigenic material, with or without the host cell or parts thereof. The virus may be treated for inactivation or attenuation. The required methods and materials to obtain avian reovirus antigenic material for the invention are standard techniques in virology, biochemistry and molecular biology, all well known to a skilled person. Nucleic acids or proteins or peptides may also be isolated from such virus strains, or produced artificially or recombinantly, and used as antigenic material.

In a particular embodiment, the antigenic material is a killed or inactivated avian reovirus. Methods of preparing inactivated viruses are well known in the art. Inactivation may be carried out by exposing the virus to a chemical agent such as formaldehyde, paraformaldehyde, b-propiolactone, ethyleneimine, binary ethyleneimine (BEI), or by derivatives thereof. Alternatively, inactivation may be carried out by physical treatments such as heat treatment or sonication. Methods of inactivation are well known to those of skill in the art. The inactivated virus may be concentrated by conventional concentration techniques, in particular by ultrafiltration, and/or purified by conventional purification means, in particular using chromatography techniques including but not limited to gel-filtration, ultracentrifugation on a sucrose gradient, or selective precipitations, in particular in PEG.

In another particular embodiment, the antigenic material is an attenuated avian reovirus, i.e., live viruses which retain immunogenic properties but are devoid of at least 70%, preferably at least 80%, even more preferably at least 90% of pathogenic properties or virulence. An attenuated virus can thus induce an immune response that protects the avian against a non-attenuated strain (i.e., a natural virulent strain) but that does not by itself cause substantial illness to the avian. In a preferred embodiment, the attenuated character indicates that the viruses, upon in vivo administration, do not cause illness to avians. Preparation of an inactivated virus may be obtained by chemical or physical means. Chemical inactivation can be effected by treating the virus strain with enzymes, formaldehyde, β-propiolactone, binary ethylene-imine or a derivative thereof. The inactivated virus so obtained may be neutralized or stabilized afterwards. Physical inactivation may be carried out by subjecting virus strain to energy-rich radiation, such as UV-light, X-radiation or γ-radiation.

The antigenic material may be derived from any avian reovirus, preferably from virulent avian reovirus.

By using a virus neutralization assay to identify new emerging isolates from chickens showing clinical signs of viral arthritis affecting the flexor tendon, the inventors have identified three new strains of avian reovirus belonging or derived to serotypes 1, 2, or 3, respectively.

The present invention therefore provides new strains of avian reovirus, designated herein strain S1 (derived to serotype 1), strain S2 (derived to serotype 2) and strain S3 (belonging to serotype 3), which exhibit strong immunogenic properties and represent valuable antigenic material for vaccination against reovirus. These strains may be used alone or in combination to prepare vaccines able to provide broad-spectrum protection against reoviruses even after only a single vaccination.

More specifically, a first strain, designated SI (Avian Reovirus 517-14), was deposited at ATCC, Patent Depository 10801 University Boulevard, Manassas, Virginia 20110-2209 USA under the terms of the Budapest Treaty, on Oct. 16, 2018, and is identified as ATCC® Patent Deposit Designation PTA-125155.

More specifically, a second strain, designated S2 (Avian Reovirus 516-14), was deposited at ATCC, Patent Depository 10801 University Boulevard, Manassas, Virginia 20110-2209 USA under the terms of the Budapest Treaty, on Oct. 16, 2018, and is identified as ATCC® Patent Deposit Designation PTA-125157.

More specifically, a third strain, designated S3 (Avian Reovirus 510-14), was deposited at ATCC, Patent Depository 10801 University Boulevard, Manassas, Virginia 20110-2209 USA under the terms of the Budapest Treaty, Oct. 16, 2018, and is identified as ATCC® Patent Deposit Designation PTA-125156.

The vaccine or composition of the invention may comprise antigenic material derived from one or several avian reoviruses. Preferably, they contain antigenic material derived from at least two different avian reovirus strains, even more preferably from at least two different avian reovirus strains of different serotypes. For instance, the antigenic material may be derived from avian reovirus selected from strains S1133, 2408, SS412, and 3005, or any combination thereof. In particular embodiment, the vaccine or composition comprises antigenic materials derived from an avian reovirus of serotype 1, an avian reovirus of serotype 2 and/or an avian reovirus of serotype 3, and/or any mixture thereof. In a particular embodiment, the vaccine or composition of the invention comprises antigenic material derived from at least one avian reovirus selected from strain S1, strain S2 and strain S3, or derivatives thereof.

In such compositions, the antigenic material from each different reovirus strain is preferably present in similar amount.

In a further particular embodiment, the vaccine or composition comprises an avian reovirus of serotype 1, an avian reovirus of serotype 2 and/or an avian reovirus of serotype 3, in killed or inactivated form. Particularly, the vaccine or composition comprises an avian reovirus selected from strains S1, S2 and S3, or derivatives thereof, in killed or inactivated form.

In another particular embodiment, the vaccine or composition comprises an avian reovirus of serotype 1, an avian reovirus of serotype 2 and/or an avian reovirus of serotype 3, in attenuated form. Particularly, the vaccine or composition comprises an avian reovirus selected from strains S1, S2 and S3, or derivatives thereof, in attenuated form.

In a further particular embodiment, the vaccine or composition comprises antigenic material derived from at least two, even more preferably at least three avian reoviruses selected from strains S1, S2 and S3, or derivatives thereof.

In another particular embodiment, the vaccine or composition of the invention comprises antigenic material derived from strains S1133 and 2408 in killed or inactivated form.

In another particular embodiment, the vaccine or composition of the invention comprises antigenic material derived from strains S1133 and 2408 in attenuated form.

Each vaccine dose may contain a suitable dose sufficient to elicit a protective immune response in avian species. Optimization of such dose is well known in the art. The amount of antigenic material per dose may be determined by known methods using antigen/anti-body reactions, for example by ELISA. Particularly, the vaccine or composition may comprise from $10^3$ $TCID_{50}$/dose to $10^9$ $TCID_{50}$/dose of at least one antigenic material as described above. Preferably, the titer of antigenic material in the vaccine is from $10^3$ $TCID_{50}$/dose to $10^7$ $TCID_{50}$/dose. In a particular embodiment, the vaccine or composition comprises from $10^3$ $TCID_{50}$/dose to $10^7$ $TCID_{50}$/dose of at least one killed avian reovirus. In a particular embodiment, the vaccine or composition comprises from $10^3$ $TCID_{50}$/dose to $10^7$ $TCID_{50}$/dose of at least one attenuated avian reovirus.

In a particular embodiment, the vaccine or composition comprises about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of killed reovirus from serotype 1, and preferably strain S1, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of killed reovirus from serotype 2, and preferably strain S2, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of killed reovirus from serotype 3, and preferably strain S3, or derivatives thereof.

In another particular embodiment, the vaccine or composition comprises about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of attenuated reovirus from serotype 1, and preferably strain S1, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of attenuated reovirus from serotype 2, and preferably strain S2, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of attenuated reovirus from serotype 3, and preferably strain S3, or derivatives thereof.

In a preferred embodiment, the vaccine or composition comprises between $10^3$ $TCID_{50}$/dose and $10^9$ $TCID_{50}$/dose of each killed reovirus strains S1, S2 and S3, or derivatives thereof. In another preferred embodiment, the vaccine or composition comprises between $10^4$ $TCID_{50}$/dose and $10^8$ $TCID_{50}$/dose of each killed reovirus strains S1, S2 and S3, or derivatives thereof. In another preferred embodiment, the vaccine or composition comprises between $10^5$ $TCID_{50}$/dose and $10^7$ TCID$_{50}$/dose of each of a killed avian reovirus strains S1, S2 and S3, or derivatives thereof.

In another preferred embodiment, the vaccine or composition comprises between $10^3$ TCID$_{50}$/dose and $10^9$ TCID$_{50}$/dose of each attenuated reovirus strains S1, S2 and S3, or derivatives thereof. In another preferred embodiment, the vaccine or composition comprises between $10^4$ TCID$_{50}$/dose and $10^8$ TCID$_{50}$/dose of each attenuated reovirus strains S1, S2 and S3, or derivatives thereof. In another preferred embodiment, the vaccine or composition comprises between $10^5$ TCID$_{50}$/dose and $10^7$ TCID$_{50}$/dose of each of an attenuated avian reovirus strains S1, S2 and S3, or derivatives thereof.

In another embodiment, the vaccine or composition comprises between $10^3$ TCID$_{50}$/dose and $10^9$ TCID$_{50}$/dose of each killed reovirus strains S1133 and 2408, or derivatives thereof. In another preferred embodiment, the vaccine or composition comprises between $10^4$ TCID$_{50}$/dose and $10^8$ TCID$_{50}$/dose of each killed reovirus strains S1133 and 2408, or derivatives thereof. In another preferred embodiment, the vaccine or composition comprises between $10^5$ TCID$_{50}$/dose and $10^7$ TCID$_{50}$/dose of each of a killed avian reovirus strains S1133 and 2408, or derivatives thereof.

In another embodiment, the vaccine or composition comprises between $10^3$ TCID$_{50}$/dose and $10^9$ TCID$_{50}$/dose of each attenuated reovirus strains S1133 and 2408, or derivatives thereof. In another preferred embodiment, the vaccine or composition comprises between $10^4$ TCID$_{50}$/dose and $10^8$ TCID$_{50}$/dose of each attenuated reovirus strains S1133 and 2408, or derivatives thereof. In another preferred embodiment, the vaccine or composition comprises between $10^5$ TCID$_{50}$/dose and $10^7$ TCID$_{50}$/dose of each of an attenuated avian reovirus strains S1133 and 2408, or derivatives thereof. It is an object of the present invention to provide a vaccine or composition as disclosed above for use for vaccinating an avian against reovirus or a reovirus-associated disease, wherein the vaccine is administered to the avian, preferably between 1 and 18 weeks of age.

A vaccine or composition according to the invention can also be combined with further antigenic material into a combination vaccine. Therefore, in an embodiment the vaccine comprises additional antigenic material that is derived from an avian pathogen. This additional antigenic material may derive from another avian reovirus, or from a distinct (different) avian pathogen. Such pathogenic microorganisms are well known in the art. For instance, the avian pathogen may be a virus selected from infectious bronchitis virus, Newcastle disease virus, avian adenovirus, avian astrovirus, avian paramyxovirus, egg drop syndrome virus, fowl adenovirus, infectious bursal disease virus, chicken anaemia virus, avian encephalo-myelitis virus, fowl pox virus, turkey rhinotracheitis virus, duck plague virus, duck viral hepatitis virus, pigeon pox virus, Marek disease virus, avian leucosis virus, infectious laryngotracheitis virus, avian metapneumovirus, avian influenza virus, and goose parvovirus.

Alternatively, the vaccine according to the invention, may itself be added to a vaccine.

As discussed above, the vaccines of the present invention advantageously contain a particular adjuvant comprising a lipophile and a polymer of acrylic or methacrylic acid. Indeed, the inventors have shown that such adjuvant is particularly advantageous for use in avian vaccine, and particularly in avian vaccines against reoviruses. This adjuvant is particularly suited for preparing a vaccine for transdermal route, and more particularly for intramuscular route.

The lipophile can be any lipophile having medium chain triglycerides. Preferably, the lipophile is selected from the group consisting of medium chain EP triglycerides, medium chain triglycerides NF, medium chain fatty acid triglyceride JPE, caprylic/capric triglyceride, and combinations thereof. The lipophile sold under the name LABRAFAC® (Gattefosse, Lyon, France), which comprises medium-chain triglycerides of caprylic and capric acids, is particularly suited.

The polymer of acrylic or methacrylic acid compound is preferably selected from the polymers of acrylic or methacrylic acid and the copolymers of maleic anhydride and alkenyl derivative. Examples of such compounds include the polymers of acrylic or methacrylic acid which are crosslinked, especially with polyalkenyl ethers of sugars or polyalcohols. These compounds are known by the term carbomer (Phameuropa Vol. 8, No. 2, June 1996). The products sold under the name CARBOPOL® (BF Goodrich, Ohio, USA), comprising carboxypolymethylene and carbomer, are particularly appropriate.

According to the invention, the adjuvant may further comprise at least one compound selected from saline, sterol, preferably cholesterol, alcohol, preferably selected from ethanol, isopropanol, butanol and combination thereof, saponin, preferably Quil A, sodium hydroxide, and any combination thereof. The saline component can be any solution of sodium chloride and water suitable for use in an adjuvant composition.

In a particular embodiment, the adjuvant comprises LABRAFAC™, cholesterol, and Quil-A. In another embodiment, the adjuvant comprises LABRAFAC™, CARBOPOL™, Saline, Cholesterol, Ethanol, Quil-A and Sodium Hydroxide. In a further embodiment, the adjuvant comprises LABRAFAC™, CARBOPOL™ 974P, Saline, vegetable-derived Cholesterol, Ethanol, Quil-A, and Sodium hydroxide. In a particular embodiment, the adjuvant comprises LABRAFAC® Lipophile WL1349 and CARBOPOL® 974P NF Polymer.

The person skilled in the art can also refer to PCT application WO2016/086222, which describes such adjuvant compositions and is thereby incorporated by reference. The products sold under the name VaxLiant ENABL® (AgriLabs, LLC (VaxLiant, LLC)), which comprise a lipophile and a polymer of acrylic and/or methacrylic acid, are particularly appropriate.

Generally speaking, an "adjuvant" is a compound or combination of compounds that enhance, activate, potentiate, or modulate the quality and/or the quantity of the immune response to an antigen.

The vaccine according to the present invention may further comprise a suitable solvent, such as for example an aqueous buffer or a phosphate buffer. Preferably, the vaccine also comprises additives. Additives of the present invention may be obtained from any of a number of sources including various proteins and peptides derived from animals (e.g., hormones, cytokines, co-stimulatory factors), and novel nucleic acids derived from viruses and other sources (e.g., double stranded RNA, CpG), and the like which are administered with the vaccine in an amount sufficient to enhance the immune response. In addition, any number of combinations of the aforementioned substances may provide an immunopotentiation effect, and therefore, can form an immunopotentiator of the present invention.

In an embodiment, the vaccine or composition can further comprise one or more stabilizers (e.g. glycine solution), and/or one or more preservatives (e.g. thimerosal solution). The preservatives can notably avoid contamination and/or bacterial growth. In a particular embodiment, the vaccine or composition further comprises glycine and thimerosal solutions.

In a particular embodiment, the vaccine or composition comprises at least one antigenic material selected from a killed avian reovirus of serotype 1, preferably strain S1, a killed avian reovirus of serotype 2, preferably strain S2, and a killed avian reovirus of serotype 3, preferably strain S3, glycine and thimerosal solutions and an adjuvant comprising a lipophile and a polymer of acrylic or methacrylic acid.

In a particular embodiment, the vaccine or composition comprises a killed avian reovirus of serotype 1, preferably strain S1, a killed avian reovirus of serotype 2, preferably strain S2 and a killed avian reovirus of serotype 3, preferably strain S3, glycine and thimerosal solutions and an adjuvant comprising a lipophile and a polymer of acrylic or methacrylic acid.

In a particular embodiment, the vaccine or composition comprises killed avian reovirus strains S1133 and 2408, glycine and thimerosal solutions and an adjuvant comprising a lipophile and a polymer of acrylic or methacrylic acid.

In a particular embodiment, the vaccine or composition comprises killed avian reovirus strains SS412, glycine and thimerosal solutions and an adjuvant comprising a lipophile and a polymer of acrylic or methacrylic acid.

In another particular embodiment, the vaccine or composition comprises at least one antigenic material derived from an avian reovirus, a pharmaceutically acceptable carrier, and an adjuvant comprising a lipophile and a polymer of acrylic or methacrylic acid.

The vaccines of the present invention may further be formulated with one or more further additives to maintain isotonicity, physiological pH and stability, for example, a buffer such as physiological saline (0.85%), phosphate-buffered saline (PBS), citrate buffers, Tris (hydroxymethyl aminomethane (TRIS)), Tris-buffered saline and the like, or an antibiotic, for example, neomycin or streptomycin.

Process for Preparing Vaccine or Composition

It is a purpose of the present invention to provide a method for preparing an avian reovirus vaccine.

It is therefore an object of the invention to provide a process for preparing a vaccine comprising at least one antigenic material derived from an avian reovirus and an adjuvant, comprising preparing the at least one antigenic material; and
adding an adjuvant comprising a lipophile and a polymer of acrylic or methacrylic acid.

In a particular embodiment, the process comprises an intermediate step of homogenously mixing the at least one antigenic material with glycine and/or thimerosal solutions, before to add the adjuvant composition.

Preferably, the antigenic material is derived from an avian reovirus selected from an avian reovirus of serotype 1, particularly strain S1, an avian reovirus of serotype 2, particularly strain S2, an avian reovirus of serotype 3, particularly strain S3, or any mixture thereof. Alternatively, the antigenic material is derived from avian reovirus selected from strains S1133, 2408, SS412, or any mixture thereof.

Method of Vaccination

Further aspects of the invention are the use of a vaccine or composition according to the invention for reducing the prevalence of avian reovirus(es) in a population or in a geographical area, a method for vaccinating avian against reoviruses, and a method for inducing an immunogenic or protective response in an avian against reoviruses. The present invention also provides method of immunizing avian species by administering an immunologically effective amount of the vaccine according to the invention.

A vaccine according to the invention can be used either as a prophylactic or as a therapeutic treatment, or both.

The route of administration can be any route including oral (e.g., gel drop, in feed, in water), ocular (e.g., by eyedrop), oculo-nasal administration using aerosol (e.g., spray), intranasal, cloacal in ovo, or by injection (e.g., intravenous, subcutaneous, intramuscular, intraorbital, intraocular, intradermal, and/or intraperitoneal) vaccination. The skilled person will easily adapt the formulation of the vaccine composition for each type of route of administration.

In a preferred embodiment, the route of administration is intramuscular route, preferably in the thigh- or breast muscle.

The scheme for the administration of a vaccine according to the invention to a target avian can be in single or multiple doses, which may be given simultaneous, concurrent or sequentially, in a manner compatible with the intended dosage and formulation, and in such an amount as will be immunologically effective. In a particular embodiment, the vaccination consists of the administration of one dose of the vaccine of the present invention ("one-dose vaccination").

Vaccination can be performed at any age. In an embodiment a vaccine according to the invention is administered to avians between 1 week and 18 weeks of age, preferably between 8 and 10 weeks, for instance at 9 weeks of age. In a particular embodiment, the vaccine is administered by intramuscular route to avians between 8 and 10 weeks of age, preferably at 8 or 9 weeks of age. Advantageously, the vaccine is administered to a dose from $10^3$ TCID$_{50}$ to $10^7$ TCID$_{50}$ of antigenic material per avian.

The present invention further relates to vaccination kits for immunizing avian species which comprises an effective amount of the vaccine as described above and a means for administering said components to said species. For example, such kit comprises an injection device filled with the vaccine according to the invention and instructions for intradermic, subcutaneous, intramuscular, or in ovo injection.

Further aspects and advantages of the invention will be disclosed in the following experimental section, which is illustrative of the claimed invention.

EXAMPLES

1. Viruses Source

The avian virus strains selected from strains S1, S2, S3, S1133 and 2408 were used in the experimental vaccine development.

2. Safety Study of Trivalent Vaccine (S1, S2, S3)

The adjuvant ENABL® P1, which comprises a lipophile and a polymer of acrylic and/or methacrylic acid, is manufactured by AgriLabs, LLC (VaxLiant, LLC) and is purchased in a ready-to-use form.

Test Serial

Reoviruses with numbers 510-14 (strain S3), 516-14 (strain S2), and 517-14 (strain S1) were used as the antigens in this study and were the same lot numbers of antigen used in the immunogenicity serial tested in all studies for reasonable expectation of efficacy. The test serial used in this study included the ENABL® P1 adjuvant at a 10-20% (v/v) final concentration. Formulation details for the test serial (trivalent vaccine) are listed in Table 1. Each chicken in the test group received 0.5 mL of this test serial into the breast muscle.

Product-Matched Placebo Serial

A product-matched placebo serial was formulated identically to the test serial except that the adjuvant component was substituted with additional glycine solution. Each chicken in the test group received 0.5 mL of this placebo serial into the breast muscle contralateral to the breast that received the test serial.

Saline Placebo

A control group received 0.5 mL sterile saline placebo in each breast for blinding purposes when evaluating the lesion scores and histopathology of the tissues.

TABLE 1

Formulation of avian reovirus vaccine test serial

| Component | Designation | Final Quantity of antigen Per Dose |
|---|---|---|
| Reovirus S1 | 517-14 | $10^5$ to $10^7$ $TCID_{50}$[1,2] |
| Reovirus S2 | 516-14 | $10^5$ to $10^7$ $TCID_{50}$ |
| Reovirus S3 | 510-14 | $10^5$ to $10^7$ $TCID_{50}$ |
| VaxLiant ENABL ® P1 | N/A[3] | 10-20% |
| Glycine Solution | N/A | N/A |
| Thimerosal Solution | N/A | N/A |

[1]$TCID_{50}$/mL = 50% tissue culture infectious dose per milliliter
[2]A final titer containing $10^5$ and $10^7$ $TCID_{50}$ per dose for each respective strain (S1, S2, S3) was in serials vaccine composition and placebo. For vaccination, 0.5 mL of the vaccine was administered to each chicken in contralateral breast muscles. Thus, there was a total antigen titer between $10^{5.5}$ and $10^{7.5}$ $TCID_{50}$ per dose per breast.
[3]NA = not applicable Protocol This study was a cross-sectional, randomized, observer-blinded, controlled trial. All SPF chickens were the same age at vaccination and collection of the respective interval samples. The study consisted of a one-dose vaccination administered by the intramuscular route (IM) route into 10-week old chickens. Two groups of SPF chickens were used; each bird in the test group were vaccinated with the test serial in a breast muscle and product-matched placebo in the contralateral muscle, and each bird of the control group received a saline placebo in a similar fashion.

Method of Vaccination

In the test group, forty-five chickens at 10 weeks of age were vaccinated by IM in the breast. One side of the breast received 0.5 mL dose of the test serial, and the other side of the breast received 0.5 mL dose of the product-matched placebo serial. A second group of fifteen chickens at 10 weeks of age received one 0.5 mL dose of saline by IM route in each breast.

Results

Safety Based on Daily Observations

No adverse reactions or mortalities were observed post-vaccination. All chickens were alive and well through necropsy.

Gross Pathology Observations

No injection site reactions were identified in any chickens in this study. All breast muscle injection site scores received a zero for all chickens from 21 to 42 days post-vaccination.

Histopathologic Observations

Microscopic lesions were not identified in sections of skeletal muscle.

Conclusion

No vaccine-related adverse or abnormal events, reactions, or mortality occurred in chickens receiving an intramuscular injection with a 0.5 mL dose of Avian Reovirus Vaccine, Killed Virus containing 10-20% (v/v) VaxLiant ENABL® P1 adjuvant. Per veterinary examination, there were no observed pathologic abnormalities or any differences between treatment groups at gross examination at 21 to 42 days post-vaccination.

3. Efficiency Study of Trivalent Vaccine

Immunogenicity Serial

Trivalent vaccine comprising killed avian reovirus strains 51, S2, and S3 combined with VaxLiant ENABL® P1 adjuvant was prepared containing between $10^5$ and $10^7$ $TCID_{50}$ of each respective strain for a total antigen titer of between $10^5$ and $10^7$ $TCID_{50}$ per 0.5 mL dose. The antigens were produced on chicken cells. Each of the antigens was concentrated following inactivation.

The reovirus antigens, glycine, and thimerosal solutions were mixed until homogenous prior to the addition of the adjuvant, ENABL® P1 (Vaxliant). The final solution was mixed until homogenous prior to aliquoting into bottles. The formulation is provided in Table 2.

TABLE 2

Formulation of the trivalent vaccine

| Component | Designation | Final Quantity Per Dose |
|---|---|---|
| Reovirus S1 | 517-14 | $10^5$ to $10^7$ $TCID_{50}$[1,2] |
| Reovirus S2 | 516-14 | $10^5$ to $10^7$ $TCID_{50}$ |
| Reovirus S3 | 510-14 | $10^5$ to $10^7$ $TCID_{50}$ |
| VaxLiant ® ENABL ® P1 | N/A[3] | 10-20% |
| Glycine Solution | N/A | N/A |
| Thimerosal Solution | N/A | N/A |

[1]$TCID_{50}$/mL = 50% tissue culture infectious dose per milliliter
[2]A final titer containing $10^5$ and $10^7$ $TCID_{50}$ per dose for each respective strain (S1, S2, S3) was in serials vaccine composition and placebo. For vaccination, 0.5 mL of the vaccine was administered to each chicken in contralateral breast muscles. Thus, there was a total antigen titer between $10^{5.5}$ and $10^{7.5}$ $TCID_{50}$ per dose per breast.
[3]NA = not applicable Placebo The same adjuvant, ENABL® P1, was used in the product-matched placebo and the antigen components were substituted with extra glycine solution. This ENABL® P1 placebo was administered at 0.5 mL per dose in the placebo-vaccinated, challenged, positive control group.

Challenge Organism

The challenge organisms were avian reovirus strains S1, S2 and S3 in virulent form.

Methods

Experimental Design

This study were randomized, double-blind, controlled trials. Fertile eggs were collected from SPF chickens from the same source (Valo, flock RF6-19) and these embryos were hatched at the same time and housed in the same room for the duration of the study. For each trial, on the day of vaccination, healthy chickens were randomly divided into three treatment groups. One treatment group was vaccinated via the intramuscular (IM) route with the trivalent vaccine and challenged; a second treatment group was vaccinated via the IM route with a product-matched placebo and challenged (placebo-vaccinated, challenged positive controls); a third treatment group was not vaccinated but challenged (non-vaccinated, challenged positive controls).

Method of Vaccination

For IM vaccination, each chicken received a dose of 0.5 mL of either trivalent vaccine or placebo administered intramuscularly at 10 weeks of age. A third treatment group did not receive a vaccine or placebo.

Method of Challenge

Chickens of all three treatment groups were challenged by footpad (right foot) injection at four weeks post vaccination (14 weeks of age) with a 0.1 mL dose of virulent homologous variant of Reovirus challenge strain S2, or
Reovirus challenge strain S1, or
Reovirus challenge strain S3.

Animals

Chickens at 10 weeks of age were used for vaccination in the study. Only healthy chickens were included. Fertile eggs were collected from SPF chickens from the same source, hatched at the same time, and housed together for the duration of the study.

Replication

At challenge, there were between twenty-eight (28) and thirty (30) replicate chickens in each of the three treatment groups.

Observations

Observation Times

Pre-Challenge

Before challenge, all chickens were observed once daily for any adverse vaccine reactions or mortality.

Post-Challenge

After challenge, chickens were observed daily for 14 days until 16 weeks of age for lesions consistent with strains S2, S1 and S3, respectively, such as swelling and discoloration of the phalangeal joint on the inoculated footpad. For each chicken on each of the 14 days, the inoculated footpad was evaluated and assigned a reovirus-induced footpad lesion score. Chickens dying during the post-challenge observation period were necropsied and evaluated for grossly observable lesions of Reovirus.

At the end of the observation period, the remaining chickens were examined for reovirus footpad lesions and euthanized.

Outcome Variables

Primary Outcome

The primary outcome was the severity of reovirus-associated footpad lesions in challenged chickens.

Severity Categorization

Severity of footpad lesions was determined by examining the right footpad of each bird on each day of the 14 day observation period. A score between zero (0) to three (3) was assigned to each footpad. The scoring system is an adaptation of the scoring system used to score reovirus injected footpads in a published study (Wu et. al, 2005). In addition, swelling observed on days 1 and 2 was disregarded as transient swelling due to the inoculation event. A score of zero (0) was assigned when there was no sign of inflammation. A score of one (1) was assigned when there was mild swelling of the inoculated side. A score of two (2) was assigned when there was severe swelling and/or discoloration of the inoculated side. A score of three (3) was assigned when there was severe swelling and signs of viremic spread up the inoculated leg and/or into the non-inoculated footpad. A footpad was protected from Reovirus challenge associated lesions if it did not display severe swelling during the 3-14 days post-challenge observations; thus, if the footpad did not receive a score of two (2) or higher for 2 or more consecutive days from 3-14 days post-challenge, it was considered protected from reovirus S2, S1 or S3 challenge strains respectively.

Results

Protection Against S2 Strain Challenge

Titration of the Challenge Virus

Three replicate virus titrations were conducted on chicken cells to determine the amount of reovirus S2 challenge administered to each chicken at 14 weeks of age. The average titer of the inoculum used in this study was between $10^2$ and $10^4$ TCID$_{50}$ per 0.1 mL footpad dose.

Observations for Mortality and Adverse Events

Chickens were observed daily for mortality and adverse events. No vaccine-related adverse events or mortality occurred during the study.

Protection Against Reovirus Strain S2

Chickens vaccinated with trivalent vaccine tended to have less severe lesions than placebo or non-vaccinated groups as indicated by 95% confidence intervals for mitigated fraction. The challenge model was proven to be clinically relevant as shown by the percent of the chickens with footpads that were scored as positive (score of 2 or higher) in the non-vaccinated and placebo-vaccinated groups, 80% and 68%, respectively, versus the trivalent-vaccinated chickens, 0% (Table 3).

TABLE 3

Clinical relevance of Reovirus S2 challenge.

| Purpose | Treatment | No. chickens positive/total | % Positive |
| --- | --- | --- | --- |
| vaccinates | trivalent vaccine | 0/30 | 0 |
| controls | placebo-vaccinated, challenged controls | 20/28 | 68 |
|  | non-vaccinated, challenged controls | 26/29 | 80 |

There were no mortalities caused by the footpad challenge. In the treatment group vaccinated with trivalent vaccine, the footpads tended to have less severe lesions than placebo-vaccinated or non-vaccinated groups.

Protection Against S1 Strain Challenge

Titration of the Challenge Virus

Three replicate virus titrations were conducted on chicken cells to determine the amount of reovirus S1 challenge administered to each chicken at 14 weeks of age. The average titer of the inoculum used in this study was between $10^2$ and $10^4$ TCID$_{50}$ per 0.1 mL footpad dose.

Observations for Mortality and Adverse Events

Chickens were observed daily for mortality and adverse events. No vaccine-related adverse events or mortality occurred during the study.

Protection Against Strain S1

Chickens vaccinated with trivalent vaccine tended to have less severe lesions than placebo or non-vaccinated groups as indicated by 95% confidence intervals for mitigated fraction. The challenge model was proven to be clinically relevant as shown by the percent of the chickens with footpads that were scored as positive (score of 2 or higher) in the non-vaccinated and placebo-vaccinated groups, 93% and 100%, respectively, versus the trivalent-vaccinated chickens, 17% (Table 4).

TABLE 4

Clinical relevance of Reovirus S1 challenge.

| Purpose | Treatment | No. chickens positive/total | % Positive |
| --- | --- | --- | --- |
| vaccinates | trivalent vaccine | 5/30 | 17 |
| controls | placebo-vaccinated, challenged controls | 28/30 | 93 |
|  | non-vaccinated, challenged controls | 30/30 | 100 |

There were no mortalities caused by the footpad challenge. In the treatment group vaccinated with trivalent vaccine, the footpads tended to have less severe lesions than placebo-vaccinated or non-vaccinated groups.

Protection Against S3 Strain Challenge

Titration of the Challenge Virus

Three replicate virus titrations were conducted on chicken cells to determine the amount of reovirus S3 challenge administered to each chicken at 14 weeks of age. The average titer of the inoculum used in this study was between $10^2$ and $10^4$ TCID$_{50}$ per 0.1 mL footpad dose.

Observations for Mortality and Adverse Events

Chickens were observed daily for mortality and adverse events. No vaccine-related adverse events or mortality occurred during the study.

Protection Against Strain S3

Chickens vaccinated with trivalent vaccine tended to have less severe lesions than placebo or non-vaccinated groups as indicated by 95% confidence intervals for mitigated fraction. The challenge model was proven to be clinically relevant as shown by the percent of the chickens with footpads that were scored as positive (score of 2 or higher) in the non-vaccinated and placebo-vaccinated groups, 63% and 73%, respectively, versus the trivalent-vaccinated chickens, 0% (Table 5).

TABLE 5

Clinical relevance of Reovirus S3 challenge.

| Purpose | Treatment | No. chickens positive/total | % Positive |
|---|---|---|---|
| vaccinates | trivalent vaccine | 0/29 | 0 |
| controls | placebo-vaccinated, challenged controls | 22/30 | 73 |
| | non-vaccinated, challenged controls | 19/30 | 63 |

There were no mortalities caused by the footpad challenge. In the treatment group vaccinated with trivalent vaccine, the footpads tended to have less severe lesions than placebo-vaccinated or non-vaccinated groups.

Conclusion

No vaccine-related adverse events or mortality occurred in chickens inoculated with trivalent vaccine of the invention. The data from this study demonstrated efficacy for a vaccine comprising between $10^5$ and $10^7$ TCID$_{50}$ per dose killed reovirus, in intramuscular vaccinated chickens against lesions caused by virulent strains S2, S1 and S3 challenge.

4. Efficiency Study of Trivalent Vaccine Against Reovirus

Challenge model studies were conducted with 8-week old SPF chickens, to determine the challenge dose for future efficacy studies with the inactivated vaccine. Table 6 describes the key points of the trials' design.

Each group of birds was housed in a separate isolator unit. Two additional chicks were added to each group as negative controls (not challenged). Each group was challenged with three different levels of challenge dose. The challenge inoculation was done in the right footpad and the footpad lesions were scored every day for the duration of 14 days post inoculation (dpi). Primary outcome of the study was the presence or absence of the footpad lesions. Conclusion criteria for an optimal challenge level was the challenge that resulted in at least 90% positive reactions.

TABLE 6

Trial Design Considerations for Footpad Challenge Model Study in 8-Week Old SPF Chickens Against Reovirus S3.

| Group Description | No. Birds per Challenge Dose | Actual Challenge range Dose/Bird | Challenge Volume |
|---|---|---|---|
| Vaccine with ENABL ® P1 Adjuvant | 15 | between $10^2$ and $10^4$ TCID50/dose | 0.1 mL |
| Non-vaccinated, challenged | 15 | between $10^2$ and $10^4$ TCID50/dose | 0.1 mL |

Both groups, vaccinates and non-vaccinated positive control birds, were comingled in the same room. The chickens were vaccinated at 8 weeks of age with 0.5 mL of inactivated vaccine by intramuscular route (IM). The birds were challenged at 12 weeks of age (4 weeks post vaccination (wpv)) with challenge level between $10^2$ and $10^4$ TCID$_{50}$ per 0.1 mL. The challenge was administered by footpad route and the footpad lesions were scored every day for the period of 14 days after challenge. Primary outcome of the study was the presence or absence of the footpad lesions. The results are shown in Table 7.

Challenge Model Studies in 8-Week-Old SPF Chickens.

Tables 7-9 show footpad lesion score data in birds that were vaccinated at 8 weeks of age with a trivalent experimental vaccine containing ENABL® P1 adjuvant and challenged 4 wpv with virulent challenge strain of reovirus strains S3, S2 and S1.

TABLE 7

Footpad Lesion Scores in SPF Chickens 6-14 Days Post Challenge (strain S3)

| Group Description | No. Birds per Challenge Dose | Challenge range Dose/Bird | No. birds pos/total | % Infection |
|---|---|---|---|---|
| Trivalent Vaccine with ENABL ® P1 Adjuvant | 15 | between $10^2$ and $10^4$ TCID50/dose | 0/15 | 0% |
| Non-vaccinated, challenged | 15 | between $10^2$ and $10^4$ TCID50/dose | 7/15 | 47% |

TABLE 8

Footpad Lesion Scores in SPF Chickens 6-14 Days Post Challenge (strain S1)

| Group Description | No. Birds per Challenge Dose | Challenge range Dose/Bird | No. birds pos/total | % Infection |
|---|---|---|---|---|
| Trivalent Vaccine with ENABL ® P1 Adjuvant | 15 | between $10^2$ and $10^4$ TCID$_{50}$/dose | 4/15 | 27% |
| Non-vaccinated, challenged | 15 | between $10^2$ and $10^4$ TCID$_{50}$/dose | 15/15 | 100% |

TABLE 9

Footpad Lesion Scores in SPF Chickens
6-14 Days Post Challenge (strain S2)

| Group Description | No. Birds per Challenge Dose | Challenge range Dose/Bird | No. birds pos/total | % Infection |
|---|---|---|---|---|
| Trivalent Vaccine with ENABL ® P1 Adjuvant | 15 | between $10^2$ and $10^4$ $TCID_{50}$/dose | 1/15 | 7% |
| Non-vaccinated, challenged | 15 | between $10^2$ and $10^4$ $TCID_{50}$/dose | 7/15 | 47% |

Conclusion

The footpad challenge model study with 8-week old chickens showed the optimal challenge dose for 8-week old chickens was $10^2$ to $10^4$ $TCID_{50}$/dose when chickens are vaccinated with the new formulation of inactivated avian reovirus vaccine containing the selected 3 strains S1, S2, and S3.

5. Safety Study of Monovalent Reovirus Vaccine

A study was conducted to confirm the safety of reovirus vaccine comprising antigenic material derived from reovirus combined with ENABL® P1 adjuvant compared to a water-in-oil adjuvant containing the same antigen. The experimental serials were made using inactivated reovirus, SS412. Traditionally reovirus vaccines are made with water-in-oil (WO) adjuvant, which is known to provide good efficiency for avian reovirus vaccines. Considering the cost of making water in oil emulsion and problem of site reaction, safety of WO adjuvant and ENABL® P1 adjuvant have been compared.

The design of this adjuvant study consisted of 3 groups as described in Table 10.

TABLE 10

Trial design considerations for different adjuvant
formulations in 9-week old SPF chickens.

| Group Description | No. birds | Vaccine Dose | Vaccine Route |
|---|---|---|---|
| WO adjuvant | 40 | $10^5$ to $10^7$ $TCID_{50}$/0.5 mL | IM |
| ENABL ® P1 adjuvant | 40 | $10^5$ to $10^7$ $TCID_{50}$/0.5 mL | IM |
| Non-vaccinated | 39 | N/A | IM |

SPF chickens were inoculated at 9 weeks of age by intramuscular route with the experimental serial containing ENABL® P1 adjuvant. Each chicken received 0.5 mL dose of the vaccine at virus titer between $10^5$ and $10^7$ $TCID_{50}$. One group remained non-vaccinated and served as negative control. At 3 and 18 weeks post vaccination (wpv) the chickens were bled and virus neutralization (VN) assay was performed using serum of the vaccinated and control chickens to evaluate serological response of the birds to the administered vaccines.

The outcome consisted of 1) injection site evaluation for reactions due to the vaccine and 2) the duration of antibodies present as determined by a virus neutralization assay. Tables 11 and 12 show the outcome of the study.

TABLE 11

Results of the injection site reaction scores

| % chickens with Injection Site Reaction Scores | WO adjuvant | ENABL ® P1 Adjuvant | Non-Vaccinates |
|---|---|---|---|
| 3 weeks post vaccination | 10% | 10% | 0% |
| 18 weeks post vaccination | 7% | 0% | 0% |

TABLE 12

Results of the virus neutralization assay

| Geometric Mean Titers | WO adjuvant | ENABL ® P1 Adjuvant | Non-Vaccinates |
|---|---|---|---|
| 3 weeks post vaccination | 4.8 | 6.7 | 0.6 |
| 18 weeks post vaccination | 8.4 | 7.3 | 0 |

The data in Table 11 shows that the vaccine with ENABL® P1 adjuvant had lower reaction scores than formulations containing WO adjuvant. At the titer between $10^5$ and $10^7$ $TCID_{50}$ antigen content per dose, the new adjuvant vaccine appeared to be safer as compared to the vaccine formulated with WO adjuvant. Additionally, the vaccine with ENABL® P1 adjuvant had a higher geometric mean titer (GMT) at 3 weeks post vaccination than the WO adjuvant, and high GMT at 18 weeks of age demonstrated high long term antibodies comparable to the WO adjuvant against reovirus SS412. These results confirm that an adjuvant comprising a lipophile and a polymer of acrylic or methacrylic acid may be efficiently used to prepare an avian reovirus vaccine showing both efficiency against reovirus infection and few side effects.

6. Study of Bivalent Vaccine (S1133, 2408)

Inactivated reoviruses strains S1133 and 2408 were used as the antigens in this study.

The vaccine used in this study included the ENABL® P1 adjuvant at a 10-20% (v/v) final concentration. Formulation details are listed in Table 13.

Each chicken in the groups B and D received 0.5 mL of the bivalent vaccine into the breast muscle. Two control groups A and C received 0.5 mL sterile saline placebo in each breast for blinding purposes when evaluating the lesion scores and histopathology of the tissues.

TABLE 13

Formulation of avian reovirus bivalent vaccine

| Component | Final Quantity of antigen Per Dose |
|---|---|
| Reovirus S1133 | $10^5$ to $10^7$ $TCID_{50}$[1,2] |
| Reovirus 2408 | $10^5$ to $10^7$ $TCID_{50}$ |
| VaxLiant ENABL ® P1 | 10-20% |
| Glycine Solution | N/A |
| Thimerosal Solution | N/A |

[1]$TCID_{50}$/mL = 50% tissue culture infectious dose per milliliter
[2]A final titer containing $10^5$ and $10^7$ $TCID_{50}$ per dose for each respective strain was in serials vaccine composition and placebo. For vaccination, 0.5 mL of the vaccine was administered to each chicken in contralateral breast muscles. Thus, there was a total antigen titer between $10^5$ and $10^7$ $TCID_{50}$ per dose per breast.

6.1 Protocol

This study was a cross-sectional, randomized, observer-blinded, controlled trial. All SPF chickens were the same age at vaccination and collection of the respective interval samples. The study consisted of a one-dose vaccination administered by the intramuscular route (IM) into 10-weeks old chickens, split into 4 groups of 21 birds each. Groups B and D were vaccinated with 0.5 mL of the bivalent S1133/2408 vaccine and groups A and C were injected with 0.5 mL of a placebo. (Table 14)

Method of Challenge

At 28 days post-vaccination, groups A and B were footpad challenged with reovirus S1133 and groups C and D were footpad challenged with reovirus 2408. The challenge dose is between $10^2$ and $10^4$ TCID50/0.1 mL.

Tests Performed

Each bird was footpad scored (both feet) and a leg weight ratio (challenge foot/placebo foot) on day 14 post-challenge. The leg weight ratio procedure was performed according to the method described in Lublin et al. (Wide-range protection against avian reovirus conferred by vaccination with representatives of four defined genotypes. Vaccine 29 (2011) 8683-8688").

An ELISA test was performed to determine the relative antibody levels within each group. Blood samples in each group A, B, C and D were collected before vaccination (6 birds per group) and before challenge (10 birds per group), and the serum was extracted.

Each sample was prepared in accordance to the instruction manual of BioChek ARV ELISA Kit (final dilution of 1:500) and pipetted on the supplied ELISA 96-well plate in duplicate. The plate was read at 404 nm and the sample to Positive (S/P) ratio values was calculated as instructed, and then each sample was averaged.

TABLE 14

Study design.

| Group | Treatment | Number of animals tested | Administration route | Quantity of vaccine injected | Vaccine dose | Challenge | Challenge dose |
|---|---|---|---|---|---|---|---|
| B | bivalent vaccine | 21 | IM | 0.5 mL | $10^5$ to $10^7$ TCID$_{50}$ | S1133 | $10^2$ to $10^4$ TCID$_{50}$/0.1 mL |
| A | Placebo | 21 | IM | 0.5 mL | | S1133 | $10^2$ to $10^4$ TCID$_{50}$/0.1 mL |
| D | bivalent vaccine | 21 | IM | 0.5 mL | $10^5$ to $10^7$ TCID$_{50}$ | 2408 | $10^2$ to $10^4$ TCID$_{50}$/0.1 mL |
| C | Placebo | 21 | IM | 0.5 mL | | 2408 | $10^2$ to $10^4$ TCID$_{50}$/0.1 mL |

6.2 Results

Safety Based on Daily Observations

No adverse reactions or mortalities were observed post-vaccination. All chickens were alive and well through necropsy.

Efficacy Results:

ELISA Results—

All samples coming from the pre-vaccination were averaged into groups A, B, C, and D. The results of the blood samples before challenge show that all birds in groups A and C were negative (S/P value≤0.199) for avian reovirus antibodies, and all birds in groups B and D were positive (S/P value≥1) for avian reovirus antibodies.

These results confirm that the vaccine induces an immune response against avian reovirus.

Leg Weight Ratios Results—

At 14 days post-challenge, both feet were removed from below the spur from each chicken and weighted. The ratio between the feet of each chicken was calculated. The groups A and C from each strain had an average ratio of 1.2 which indicates a measureable difference between the challenged and unchallenged feet of the placebo vaccinated chickens. The groups B and D from each strain had an average ratio of 1.0 which indicates there is no difference between the challenged and unchallenged feet of the vaccinated chickens. The mitigated fraction with a 95% confidence interval showed all confidence intervals are above zero, indicating the vaccine is effective as shown by the leg weight ratio at 14 days post challenge of the vaccinated as compared to the placebo groups.

6.3 Conclusion

It was found that the vaccinated birds for S1133 and 2408 were 95% and 90% protected by footpad challenge and the leg weight ratios indicated significant protection of the vaccinates compared to the placebo-vaccinated chickens. The ELISA results showed that a vaccine comprising avian reovirus strains S1133 and 2408 and an adjuvant comprising lipophile and a polymer of acrylic or methacrylic acid permits to induce an immune response against reovirus S1133 and 2408 challenge.

What is claimed is:

1. A vaccine comprising at least one antigenic material derived from an avian reovirus selected from avian reovirus designated strain S1, a sample of which is deposited at the ATCC under accession number PTA-125155 (S1), avian reovirus designated strain S2, a sample of which is deposited at the ATCC under accession number PTA-125157 (S2), avian reovirus designated strain S3, a sample of which is deposited at the ATCC under accession number PTA-125156 (S3), or any derivative thereof and an adjuvant comprising a lipophile and a polymer of acrylic or methacrylic acid.

2. The vaccine of claim 1, wherein the polymer of acrylic or methacrylic acid is a carbomer.

3. The vaccine of claim 1, wherein the lipophile is selected from the group consisting of medium chain EP triglycerides, medium chain triglycerides NF, medium chain fatty acid triglyceride JPE, caprylic/capric triglyceride, and combinations thereof.

4. The vaccine of claim 1, wherein the adjuvant further comprises at least one compound selected from saline, sterol, alcohol, saponin, sodium hydroxide, and any combination thereof.

5. The vaccine of claim 1, wherein the antigenic material comprises an inactivated avian reovirus.

6. The vaccine of claim 1, comprising antigenic materials derived from at least two distinct avian reovirus strains.

7. The vaccine of claim 1, wherein the antigenic material is derived from at least two reoviruses selected from strain S1, strain S2 and strain S3, or any derivative thereof.

8. The vaccine of claim 1, wherein the antigenic material is derived from strain SI, strain S2 and strain S3, which are present in similar amounts.

9. The vaccine of claim 1, wherein the vaccine comprises from $10^3$ TCID$_{50}$/dose to $10^9$ TCID$_{50}$/dose of the at least one avian reovirus antigenic material.

10. The vaccine of claim 1, wherein the vaccine comprises from $10^3$ TCID$_{50}$/dose to $10^9$ TCID$_{50}$/dose of an inactivated avian reovirus selected from strain S1, strain S2, and strain S3.

11. The vaccine of claim 1, wherein the vaccine comprises additional antigenic material from a distinct avian pathogen.

12. The vaccine of claim 1, further comprising a pharmaceutically acceptable carrier.

13. A vaccine comprising at least one antigenic material derived from an avian reovirus selected from avian reovirus designated strain S1, a sample of which is deposited at the ATCC under accession number PTA-125155 (S1), avian reovirus designated strain S2, a sample of which is deposited at the ATCC under accession number PTA-125157 (S2), avian reovirus designated strain S3, a sample of which is deposited at the ATCC under accession number PTA-125156 (S3), and an adjuvant.

14. A process for preparing a vaccine comprising at least one antigenic material derived from an avian reovirus selected from avian reovirus designated strain S1, a sample of which is deposited at the ATCC under accession number PTA-125155 (S1), avian reovirus designated strain S2, a sample of which is deposited at the ATCC under accession number PTA-125157 (S2), avian reovirus designated strain S3, a sample of which is deposited at the ATCC under accession number PTA-125156 (S3), and an adjuvant, comprising preparing the at least one antigenic material; and adding an adjuvant comprising a lipophile and a polymer of acrylic or methacrylic acid.

15. The process of claim 14, further comprising a step of homogenously mixing the at least one antigenic material with glycine and thimerosal solutions, before adding the adjuvant.

16. A method for vaccinating an avian against reovirus, comprising administering to the avian a vaccine of claim 1.

* * * * *

UNITED STATES PATENT AND TRADEMARK OFFICE
CERTIFICATE OF CORRECTION

| | | |
|---|---|---|
| PATENT NO. | : 11,813,321 B2 | Page 1 of 1 |
| APPLICATION NO. | : 17/259798 | |
| DATED | : November 14, 2023 | |
| INVENTOR(S) | : Kristi Mae Dorsey et al. | |

It is certified that error appears in the above-identified patent and that said Letters Patent is hereby corrected as shown below:

In the Specification

<u>Column 13,</u>
Line 2, "strain 51" should read --strain S1--.

Signed and Sealed this
Twenty-first Day of May, 2024

Katherine Kelly Vidal
*Director of the United States Patent and Trademark Office*